United States Patent
Mitchell

(10) Patent No.: US 7,663,751 B1
(45) Date of Patent: Feb. 16, 2010

(54) NEPHELOMETER INSTRUMENT FOR MEASURING TURBIDITY OF WATER

(76) Inventor: Herbert Leckie Mitchell, 656 Independence Valley Dr., Grand Junction, CO (US) 81507

( * ) Notice: Subject to any disclaimer, the term of this patent is extended or adjusted under 35 U.S.C. 154(b) by 0 days.

(21) Appl. No.: 12/378,008

(22) Filed: Feb. 10, 2009

(51) Int. Cl.
*G01N 21/00* (2006.01)

(52) U.S. Cl. ...................................... 356/339

(58) Field of Classification Search ......... 356/335–343, 356/432–440
See application file for complete search history.

(56) References Cited

U.S. PATENT DOCUMENTS

| | | | |
|---|---|---|---|
| 4,826,319 A | 5/1989 | Namba et al. | |
| 5,250,186 A | 10/1993 | Dollinger et al. | |
| 5,332,905 A * | 7/1994 | Brooker et al. | 250/458.1 |
| 5,872,361 A | 2/1999 | Paoli et al. | |
| 5,969,814 A | 10/1999 | Barber et al. | |
| 6,842,243 B2 | 1/2005 | Tokhtuev et al. | |
| 7,029,628 B2 * | 4/2006 | Tam et al. | 422/68.1 |
| 7,242,001 B1 | 7/2007 | Hedges et al. | |
| 7,491,366 B2 * | 2/2009 | Tokhtuev et al. | 422/82.05 |
| 2007/0127021 A1 * | 6/2007 | Dal Sasso et al. | 356/319 |
| 2008/0137080 A1 * | 6/2008 | Bodzin et al. | 356/300 |

* cited by examiner

*Primary Examiner*—Hoa Q Pham

(57) ABSTRACT

The specific wavelength of 525 nm is described as a single monochromatic light source used in the determination of turbidity by nephelometry at 90° for particulate matter in raw water, water treatment, waste water treatment and industrial process streams. This wavelength improves the detection of smaller particle concentration in water where light scattering characteristics of shorter wavelengths are superior to light sources using longer wavelengths.

2 Claims, 1 Drawing Sheet

NEPHELOMETER INSTRUMENT FOR MEASURING TURBIDITY OF WATER

TECHNICAL FIELD

Figure 1:
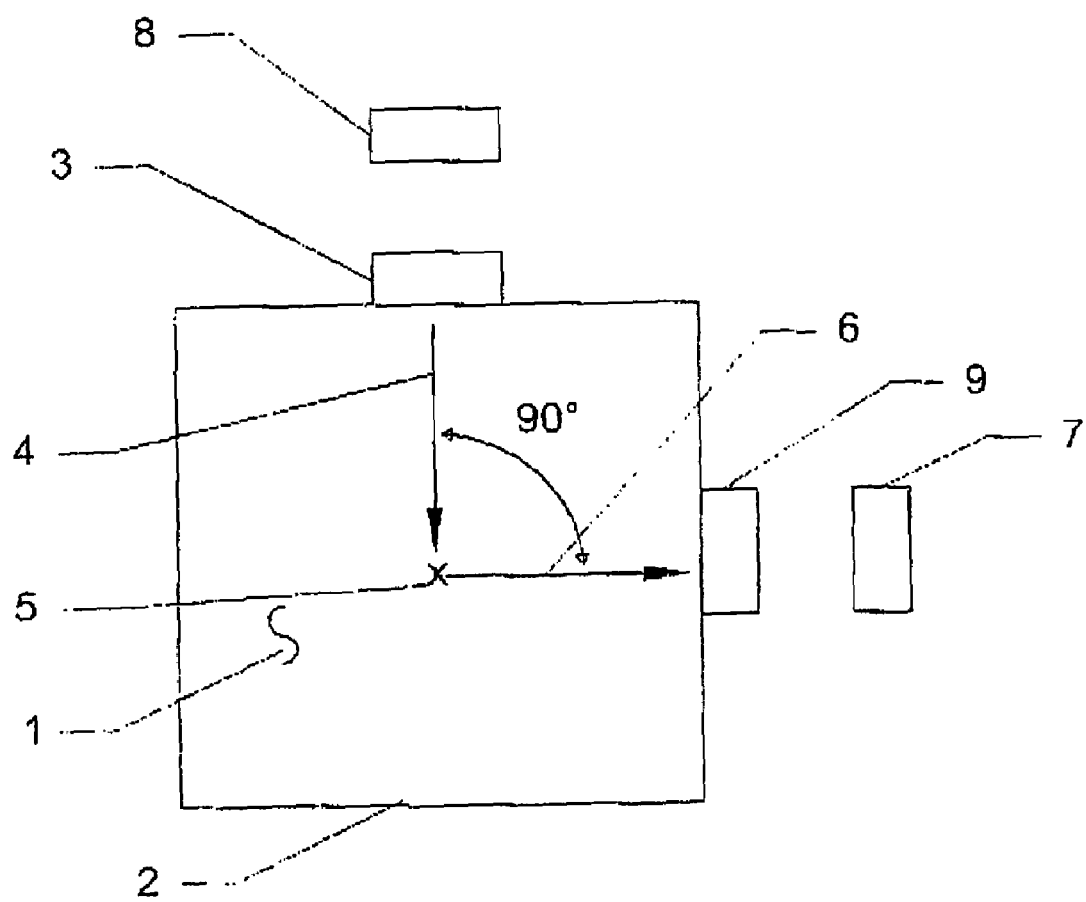

Nephelometric turbidimeters are used to monitor on-line streams in raw water, water treatment plants, waste water treatment plants, and process streams requiring detection of particle concentration. The different wavelengths of the light-source beams have varying abilities and characteristics in the detection of multiple sizes of particles in a fluid concentration. A specific single monochromatic light source wavelength of 525 nm improves the detection of smaller particle concentration and is embodied in the turbidimeter. Scattering characteristics of said wavelength are superior to light sources using longer wavelengths.

BACKGROUND

Turbidity comes from the Greek word turbid while nephelometry is the optical measurement of scattered light and is the Greek word for cloud. In water treatment plants the required detection limit is approximately one part per million of particles with a detectable change of one part per billion of particles and is read in Nephelometric Turbidity Units (NTU). The specifications required for monitoring of water is set by each country, but all are similar in their quality control characteristics and performance. The cloudiness is caused by particle concentrations in the fluid which may be organic material, clay, sand or other particulate matter. In water treatment plants this measurement provides: (1) a measurement of filter effectiveness and (2) a surrogate method for determining the level of microbial contaminates embedded in the particulate matter in the incoming raw water and any microbial remnants in the filtered water. The greater the concentration of particles in the fluid, or turbidity, the higher the level of microbial contaminates embedded in the particles and the higher the required level of disinfection procedures. Treatment water plants walk a thin line between too little disinfection in protecting the community from harmful microbes and too much disinfection causing harm from disinfection by-products. Nephelometric turbidity is the workhorse of all water treatment plants. There are essentially three ways to optically measure turbidity:

1. Forward-scatter follows Lambert-Beers Law; the light source and detector are≈180° apart;
2. Side-scatter follows Rayleigh Scattering and is an EPA nephelometric turbidity specification; the light source and detector are 90° apart;
3. Back-scatter measures reflectance of light opposite to the incident radiation; approximately 2 to 40 degrees separate the light source from the detector; the light scattering is measured as it folds back on itself.

EPA nephelometric specifications require side-scatter measurement at 90° with mandated wavelengths between 400 nm and 600 nm (unless otherwise approved) for the light source, with no more than a 10 cm light path length. The light source must maintain a color temperature between 2200° and 3000° K. These specifications are required by EPA 180.1 Methods for federal regulations in the *Determination of Turbidity by Nephlometery* for water and waste water treatment plants reporting turbidity to the EPA (There is a better response at these wavelengths to smaller concentrations of turbidity in colorless water).

In order to satisfy the various wavelength requirements specified by different government agencies, a number of light sources have been approved for nephelometric turbidity measurement and reporting:

| USEPA 180.1-1 | Incandescent | 2200-3000K Originai (blackbody) |
| USEPA 180.1-2 | LED | 860 nm GLI 4-beam, |
| USEPA 180.1-3 | Laser | 660 nm with photomultiplier tube |
| USEPA 180.1-4 | LED | 525 nm (Mitchell Method M5331) |
| USEPA 180.1-5 | Laser | 660 nm (Mitchell Method M5271) |

Note: the two Mitchell Methods were EPA approved and published in the Federal Register on Aug. 3, 2009.

| ISO 7027 basic | LED | 860 nm International |
| ISO 7027 alternate | LED | 550 nm International |

In a review of light source literature, patents and regulations there are references to laser, LED, and incandescent for USEPA 180.1 specification of Methods and for ISO 7027 specification of Methods: USEPA 180.1-1 specifies an incandescent source of 2200-3000° K.; USEPA 180.1-2 specifies 860 nm dual sources using the same wavelength; USEPA 180.1-3 specifies 660 nm using a photomultiplier tube; ISO 7027 specifies 860 nm with an alternate 550 nm; U.S. Pat. No. 5,969,814 mentions 670 nm; U.S. Pat. No. 7,242,001 mentions 880 nm while U.S. Pat. No. 4,826,319 has 633 nm specified. U.S. Pat. No. 5,250,186 discusses the use of 633 nm and 467 nm.

SUMMARY

The light source proposed for use in nephelometric turbidity measurement at 90° of raw water; water treatment plants; waste water treatment plants and in industries using process streams is a single monochromatic, solid-state, light source operating at 525 nanometers. This shorter wavelength provides superior detection capability over other light sources previously approved and used in USEPA 180.1-1-2-3 and ISO 7027 specifications for methods of monitoring nephelometric turbidity.

FIGURE NUMBER OF THE DRAWING WITH DESCRIPTION

FIG. 1 depicts light source 8 which generates light source beam 4. Light source beam 4 is transmitted through window 3 into fluid 1 in container 2 where it strikes particle 5 resulting in scattered light beam 6 which goes through window 9 and into detector 7.

REFERENCE NUMBERS WITH DESCRIPTION 1. fluid
2. container
3. window
4. source light beam
5. particle
6. scattered light beam
7. detector
8. light source at 525 nm
9. window

DETAILED DESCRIPTION

In a nephelometric turbidimeter, a beam of light is scattered by particles having a different refractive index than the suspending medium. The scattered light is detected at 90° and is a measure of the particle concentration. This Rayleigh scattering is affected by the wavelength of the source light. The scattering effect is 1/wavelength to the $4^{th}$ power. The use of a single monochromatic light source is described which operates at 525[±15] nanometers providing a stable beam with minimal effect. This wavelength offers a 20% increase is scattered light and detection capability over the ISO 7027 short wave of 550 nm; over 2.5 times increase over USEPA 180.1-3 using 660 nm, and seven times increase over ISO 7027 long wave 860 nm and EPA 180.1-2 at 860 nm. The use of a solid state monochromatic source at 525 nm provides superior life, lower cost, greater reliability and stability and greater sensitivity to low-particle concentrations than the current USEPA 180.1-1, Method (incandescent.) If the wavelength is not tightly specified, a large variation will result in the scattered light pattern and in the instrumentation's response to small particles. For example, if the light source's wavelength is specified between 400 nm and 600 nm, there is a Rayleigh scattering variation of five to one. In EPA 180.1 incandescent, the color temperature is allowed to vary between 2200-3000° K, which shifts the peak output of the source over a wide range. This variation changes the instrumentation's response to small particles. A single monochromatic source solves these problems and provides a repeatable reading. LED and laser are essentially stable light sources.

It is an object to improve nephelometric turbidimeters for use in particle concentration detection and monitoring in raw water, water treatment plants, waste water treatment plants and in industries using process streams.

It is an object to provide a nephelometric turbidimeter with a superior light source.

Other advantages and features of novelty which characterize this specific light source for use in nephelometric turbidity monitoring will be apparent to those skilled in the art upon reviewing the particularity in the claims.

What is claimed is:

1. A nephelometric device for measuring turbidity comprises:
    a single monochromatic light source having a light beam for illuminating the raw water, water treatment, waste water treatment and industrial process streams, wherein the light source having substantially a single wavelength of 525 nm; a detector located perpendicular to the light beam for collecting scattered light by the particles in said raw water, water treatment, waste water treatment and industrial process streams; and
    means for monitoring particle concentration and turbidity of said water.

2. A device according to claim 1, said light source is selected from a group consisting of: a laser, an Organic Light Emitting Diode (OLED); and a Light Emitting Diode (LED).

* * * * *